United States Patent [19]
Cantin et al.

[11] Patent Number: 5,922,764
[45] Date of Patent: Jul. 13, 1999

[54] STABLE GELLED COMPOSITION WITH A HIGH ELECTROLYTE CONTENT

[75] Inventors: Herve Cantin, Morangis; Didier Gagnebien, Chatillon, both of France

[73] Assignee: L'Oreal, Paris, France

[21] Appl. No.: 08/787,604

[22] Filed: Jan. 23, 1997

[30] Foreign Application Priority Data

Jan. 23, 1996 [FR] France .................................. 96 00742

[51] Int. Cl.[6] ................................................... A61K 31/19
[52] U.S. Cl. ............................................ 514/557; 514/781
[58] Field of Search ..................................... 514/557, 781

[56] References Cited

U.S. PATENT DOCUMENTS

| | | |
|---|---|---|
| 4,228,277 | 10/1980 | Landoll . |
| 4,352,916 | 10/1982 | Landoll . |
| 4,618,491 | 10/1986 | Kanematu et al. . |
| 4,892,589 | 1/1990 | Kirkland et al. . |
| 5,382,432 | 1/1995 | McCook et al. ........................ 514/844 |

FOREIGN PATENT DOCUMENTS

| | | |
|---|---|---|
| 0 654 270 A1 | 5/1995 | European Pat. Off. . |
| 3421 443 A1 | 12/1985 | Germany . |
| 9-87130 | 3/1997 | Japan . |
| WO 93/16683 | 9/1993 | WIPO . |

OTHER PUBLICATIONS

J. J. De Bruin, "Hydrophobically Modified Cellulose Ethers for Personal Care", Seifen, Ole, Fette, Wachse Journal, vol. 120, No. 15, pp. 944–948, 1994.
Chemical Abstracts 119:210260 (1993). Alban et al.
Chemical Abstracts 127:23556 (1995). Wantanabe et al.

*Primary Examiner*—Zohreh Fay
*Attorney, Agent, or Firm*—Oblon, Spivak, McClelland, Maier & Neustadt, P.C.

[57] ABSTRACT

A gel composition containing an at least one cosmetic and/or dermatological active agent, at least one electrolyte, cetyl-hydroxyethyl cellulose and water. The composition is useful for treating the skin, scalp, hair, mucous membranes and/or nails.

21 Claims, No Drawings

STABLE GELLED COMPOSITION WITH A HIGH ELECTROLYTE CONTENT

BACKGROUND OF THE INVENTION

1. Field of the Invention

The present invention is directed to a gel composition containing at least one cosmetic and/or dermatological active agent, at least one electrolyte, cetylhydroxyethyl cellulose and water useful for treating the skin, scalp, hair, mucous membranes and/or nails.

2. Discussion of the Background

Topical compositions in the form of an aqueous gel or emulsion are well-known in the cosmetic, dermatological and pharmaceutical fields. These compositions contain gelling agents which impart consistency and stability to the gel. Most of the gelling agents currently used are carboxyvinyl polymers, which are neutralized with a base. However, some materials cannot be used in these compositions because they are incompatible with carboxyvinyl polymer gelling agents. For example, electrolytes, i.e., inorganic or organic salts, are incompatible with neutralized carboxyvinyl polymers because they "break" the emulsion and liquefy it. As a result, these compositions have an unsightly appearance.

Electrolytes are particularly desirable components of thickened, topical gel compositions when they have a beneficial effect on the skin or hair and are used in combination with cosmetic and/or dermatological active agents. Electrolytes are particularly useful in gel compositions where the active agents have an irritant side effect when applied alone because they may reduce the irritating nature of these active agents. The gelling agent should be compatible with the electrolytes while preserving the efficacy of the active agent and the electrolytes. In addition, gel compositions for topical application are preferably clear and stable.

Polysaccharide-type gelling agents, such as guar gums, xanthan gums and cellulose derivatives, have been used in place of carboxyvinyl polymers. EP-A-654270 describes a topical composition intended for the treatment of acne and seborrhoeic dermatitis containing a mixture of salts and hydroxyethyl cellulose as the gelling agent. However, these compositions, especially aqueous gels containing no oily phase, have an unsightly lumpy appearance. In addition, they leave the skin "wet looking" after application because these compositions do not penetrate sufficiently into the skin. Therefore, these materials have limited use as cosmetics and/or dermatological agents, where product appearance is critical. The combination of these cellulose derivatives with another thickening agent, such as a silicate as described in WO-A-93/8230, provides compositions with the same disadvantages.

Seifen, Ole, Fette, Wachse Journal, vol. 120, No. 15, 1994 describes the use of hydrophobically modified hydroxyethyl cellulose in compositions for skin care and the compatibility of this material with various types of salts. However, these compositions do not contain cosmetic active agents. In addition, there is no suggestion of a clear and stable gel composition containing cetylhydroxyethyl cellulose, active agents and a large quantity of electrolyte.

Therefore, the need remains for gel compositions which overcome the disadvantages of known gelling agents: lack of consistency, instability, lumpy appearance, unpleasant sensation to the touch and incompatibility with electrolytes.

The present Applicants have now unexpectedly found that cetylhydroxyethyl cellulose stabilizes gel compositions containing active agents and large quantities of electrolyte.

SUMMARY OF THE INVENTION

An object of the present invention is to provide a stable gel composition containing a cosmetic and/or dermatological active agent and electrolyte which has a pleasant feeling when applied to the skin, scalp, hair, mucous membranes and/or nails.

Another object of the present invention is to provide a stable gel composition containing a large quantity of electrolyte.

Another object of the present invention is to provide a gel composition useful for treating the skin, scalp, hair, mucous membranes and/or nails.

Another object of the present invention is to provide a gel composition useful for treating the skin, scalp, hair, mucous membranes and/or nails of a sensitive subject.

Another object of the present invention is to provide a gel composition useful for treating sensitive skin and/or sensitive scalp.

Another object of the present invention is to provide a gel composition useful for moisturizing the skin.

Another object of the present invention is to provide a gel composition useful for combating the visible signs of skin aging.

Another object of the present invention is to provide a method of treating the skin, scalp, hair, mucous membranes and/or nails.

Another object of the present invention is to provide a method of treating sensitive skin and/or sensitive scalp.

Another object of the present invention is to provide a method of moisturizing the skin.

Another object of the present invention is to provide a method of combating the visible signs of skin aging.

These objects and others may be accomplished with a gel composition containing at least one cosmetic and/or dermatological active agent, at least one electrolyte, cetylhydroxyethyl cellulose and water.

The above objects may also be accomplished with a gel composition additionally containing a dispersed oil.

The above objects may also be accomplished with a gel composition additionally containing an oily phase.

The objects above may also be accomplished by a method of treating the skin, scalp, hair, mucous membranes and/or nails by applying a gel composition to the skin, scalp, hair, mucous membranes and/or nails of a subject, where the gel composition contains at least one cosmetic and/or dermatological active agent, at least one electrolyte, cetylhydroxyethyl cellulose and water.

The above objects may also be accomplished with a processing of manufacturing a cosmetic and/or dermatological composition by combining at least one cosmetic or dermatological active agent, at least one electrolyte cetylhydroxyethyl cellulose and water to produce a gel.

DETAILED DESCRIPTION OF THE INVENTION

A more complete appreciation of the invention and many of the attendant advantages thereof will be readily obtained as the same becomes better understood by reference to the following detailed description.

The present invention is directed to a topical gel composition containing an at least one cosmetic and/or dermatological active agent, at least one electrolyte, cetylhydroxyethyl cellulose and water. The term "gel composition"

includes an aqueous gel, an aqueous-alcoholic gel, a water-in-oil emulsion and an oil-in-water emulsion. The term "aqueous gel" or "aqueous-alcoholic gel" includes aqueous or aqueous-alcoholic gel composition additionally containing a dispersed oil, other fatty substance and/or an emulsifier.

Cetylhydroxyethyl cellulose is used as a gelling agent in the present composition. Cetylhydroxyethyl cellulose is the ether of cetyl alcohol and hydroxyethyl cellulose. It may be prepared by by step-wise or simultaneous reaction of ethylene oxide and a cetylating reagent (such as cetyl bromide) and cellulose. The cetylhydroxyethyl cellulose is preferably water-soluble. The degree of cetyl substitution is preferably 0.1 to 4.0%, more preferably 0.2 and 1.2, and most preferably 0.4 to 0.9% by weight of the polymer. The hydroxyethyl molar substitution is preferably 1.5 to 4, more preferably 2 to 3.7, and most preferably 2.5 to 3.7. The average molecular weight prior to cetyl modification is preferably 20,000 to 800,000, more preferably 20,000 to 500,000, and most preferably 20,000 to 400,000. All of the ranges described above explicitly include all specific values and subranges therebetween. A particularly preferred and commercially available source of cetylhydroxyethyl cellulose is POLYSURF 67, available from Aqualon Company, Wilmington, Del. Cetylhydroxyethyl cellulose may be used in a quantity ranging from 0.1 to 10%, preferably from 0.5 to 3%, more preferably from 0.5 to 2% and most preferably 0.5 to 1.5% by weight, based on the total weight of the composition. These ranges include all specific values and subranges therebetween, including 0.2, 0.4, 0.75, 1, 1.25, 1.75, 2.25 and 2.75% by weight. Cellulose ethers are broadly disclosed in *Kirk-Othmer Encyclopedia of Chemical Technology*, Volume 5, Fourth Edition, 1993, pages 541–563, U.S. Pat. No. 4,228,277, U.S. Pat. No. 4,352,916 and U.S. Pat. No. 4,892,589, all incorporated herein by reference.

The term "electrolyte" includes inorganic salts. Preferred electrolytes are salts of mono-, di- or trivalent metal ions. More preferred electrolytes are salts of alkaline earth metals (beryllium, magnesium, calcium, strontium and barium), salts of alkali metals (such as lithium, sodium and potassium) or salts of yttrium, lanthanum, cerium, praseodymium, neodymium, promethium, samarium, europium, gadolinium, terbium, dysprosium, holmium, erbium, thulium, ytterbium, lutetium, tin, zinc, manganese, cobalt, nickel, iron, copper, rubidium, aluminum, silicon and selenium. A strontium or neodymium salt is most preferred.

The anions of these salts may be carbonates, bicarbonates, sulfates, glycerophosphates, borates, chlorides, nitrates, acetates, hydroxides, persulfates, α-hydroxy acid carboxylates (such as citrates, tartrates, lactates, malates), fruit acid carboxylates or carboxylates of amino acids (such as aspartate, arginate, glycocholate and fumarate).

Preferably, the electrolyte is calcium nitrate, manganese nitrate, strontium nitrate, calcium borate, magnesium borate, calcium chloride, sodium chloride, magnesium chloride, strontium chloride, neodymium chloride, manganese chloride, magnesium sulfate, calcium sulfate, calcium acetate, magnesium acetate or mixtures thereof.

The electrolyte may be present in the composition in any quantity ranging from 0.5 to 40%, preferably from 1 to 20% by weight, based on the total weight of the composition. There ranges include all specific values and subranges therebetween, including 0.75, 2, 3, 5, 8, 10, 11, 12, 15, 25, 30 and 35% by weight.

The term "active agent" includes any substance having a cosmetic or dermatological effect when applied to the skin, scalp, hair, mucous membranes or nails. The active agent is preferably an antibacterial, antiparasitic, antifungal, antiviral, anti-inflammatory, antipruritic, anesthetic, keratolytic, anti-free radical, antiseborrhoeic, antidandruff, antiacne and antiseptic agents, an agent for reducing the signs of aging and/or the agents modulating skin differentiation and/or proliferation and/or pigmentation or a vitamin (such as vitamin C).

More preferable active agents include α-hydroxy acids, β-hydroxy acids, α-keto acids, β-keto acids, retinoids (such as retinol, retinal and retinoic acid), anthralins (such as dioxyanthranol), anthranoids, the peroxides (such as benzoyl peroxides), minoxidil, lithium salts, antimetabolites or vitamin D and derivatives thereof. Some of these active agents may have an irritant side effect when applied directly to the skin, scalp, hair mucous membranes or nails. One advantage of the present gel composition is that these active agents may be used to treat sensitive subjects, particularly subjects with sensitive skin and/or scalp.

Preferable α-hydroxy acids are citric, malic, glycolic, tartaric, mandelic and lactic acid. Preferable β-hydroxy acids are salicylic acid and acylated derivatives thereof, 2-hydroxyalkanoic acids and derivatives thereof (such as 2-hydroxy-3-methylbenzoic acid and 2-hydroxy-3-methoxybenzoic acid). Preferable salicylic acid derivatives are described in FR-A-2,581,542 and EP-A-378936, both incorporated herein by reference, and include 5-n-octanoylsalicylic, 5-n-decanoylsalicylic, 5-n-dodecanoylsalicylic, 5-n-octylsalicylic, 5-n-heptyloxysalicylic and 4-n-heptyloxysalicylic acids. The salicylic acid derivatives described in EP-A-570230, incorporated herein by reference, may also be used.

Other active agents that may be used in the gel composition wich have an irritant side effect include colorants (such as para-phenylenediamine and derivatives thereof and aminophenols), perfuming alcoholic solutions (such as perfumes, toilet waters, aftershaves and deodorants), antiperspirant agents (such as aluminum salts), depilatory or permanent waving active agents (such as thiols), depigmenting active agents (such as hydroquinone), pigments, surfactants and chemical screening agents. Some of these active agents may be irritating or sensitizing to a greater or lesser degree, depending on the quantity used and the sensitivity of the subject.

The amount of active agent in the composition may vary widely depending on the nature and function of the active agent. The gel preferably contains 0.001 to 30%, more preferably 0.05 to 20% and most preferably 0.1 to 10% by weight of active agent. These ranges include all specific values and subranges therebetween, including 0.005, 0.01, 0.05, 0.1, 0.5, 1, 2, 5, 10, 15, 20 and 25% by weight.

The present composition may contain 20 to 99.4% by weight water. Preferably, the active agent, electrolyte, cetylhydroxyethyl cellulose and water comprise an aqueous phase. Preferably, the aqueous gel has a clear appearance. The viscosity of the gel is preferably greater than a few poises and, more preferably, between 4 and 6 poise. Most preferably, the viscosity is between 5 to 6 poise (equivalent to 0.5 to 0.6 Pa·s).

The composition may also contain a topically acceptable medium. The medium is preferably compatible with the skin, scalp, hair, mucous membranes and/or nails. The composition may be in any galenical form appropriate for topical application. Preferred forms are an aqueous gel, an aqueous-alcoholic gel, a water-in-oil or an oil-in-water emulsion or an aqueous suspension containing ionic and/or nonionic lipid vesicles. The quantities of materials in the present gel are those well-known to those of ordinary skill in the cosmetic and dermatological arts. The present composition may be in the form of a serum, a cream or a milk.

When the composition is an emulsion it also contains an oily phase, in addition to the aqueous phase. The proportion of the oily phase may be 5 to 80% by weight and preferably 5 to 50% by weight, based on the total weight of the composition. More preferably, the emulsion contains 5 to 35% by weight and, most preferably, 10 to 30% by weight of the oily phase. These ranges include all specific values and subranges therebetween. Preferably, the oily phase contains oils and/or other fatty substances. The oily phase may also contain emulsifiers and coemulsifiers. The oils, fatty substances, emulsifiers and coemulsifiers used in the composition are chosen from those conventionally used in the cosmetic and dermatologic fields. The oily phase may also contain one or more active agents. The emulsion may also contain lipid vesicles.

Preferable oils are mineral oils (such as hydrogenated isoparaffin), vegetable oils (such as apricot oil), animal oils, synthetic oils (such as pentaerythrityl tetraethylhexanoate), silicone oils (such as cyclomethicone) and fluorinated oils. Other fatty substances which may be used in the oily phase include fatty alcohols (such as cetyl alcohol), fatty acids, waxes and waxy compounds (such as copra fatty acid diethanolamine) and hydrophobic gums (such as silicone gum). Oils and other fatty substances which may be used in the present composition are disclosed in *Kirk-Othmer Encyclopedia of Chemical Technology*, Volume 7, Fourth Edition, 1993, pages 572–619, incorporated herein by reference.

Preferable emulsifiers are the mixture of glyceryl monostearate and polyethylene glycol stearate sold as ARLACEL 165 by ICI Surfactants, Wilmington, Del., sorbitan tristearate sold by ICI Surfactants as SPAN 65, PEG-40 stearate sold by ICI Surfactants as MYRJ 52, cetyl dimethicone copolyol sold by the Goldschmidt Chemical Corporation, Hopewell, Va., as ABIL EM-90. Other emulsifiers that may be used in the present composition are disclosed in *Kirk-Othmer Encyclopedia of Chemical Technology*, Volume 7, Fourth Edition, 1993, pages 572–619. The emulsifier and the coemulsifier may be present in the composition in an amount ranging from 0.3 to 30% by weight, and preferably from 0.5 to 20% by weight, based on the total weight of the composition. These ranges include all specific values and subranges therebetween.

The aqueous or aqueous-alcoholic gel may also contain a dispersed oil or other fatty substance. Preferably, the dispersed oil or other fatty substance comprises 0.1 to 2%, more preferably 0.2 to 1.5%, and most preferably 0.5 to 1% by weight of the composition. The aqueous or aqueous-alcoholic gel may also contain one or more emulsifiers or coemulsifiers. Preferably, the composition contains 0.05 to 1%, more preferably 0.1 to 0.5%, and most preferably 0.2 to 0.4% by weight emulsifier or coemulsifier. Suitable oils, fatty substances, emulsifiers and coemulsifiers are described above.

The present gel composition may also contain adjuvants which are well-known to those of ordinary skill in the cosmetic and/or dermatological fields. Preferable adjuvants are moisturizing agents (such as glycerin, the sodium salt of pyrrolidonecarboxylic acid and D-panthenol), preservatives, antioxidants, complexing agents, solvents, perfumes, fillers, screening agents, bactericides, odor absorbers and coloring matter. Other examples of these adjuvants are disclosed in *Kirk-Othmer Encyclopedia of Chemical Technology*, Volume 7, Fourth Edition, 1993, pages 572–619. The amount of adjuvant in the composition may vary widely. Preferably, the composition contains 0.01 to 20% by weight of adjuvant. This range includes all specific values and subranges therebetween. The adjuvant may be present in the aqueous phase, the oily phase and/or the lipid vesicles.

The present gel composition may be used for treating and caring for the skin, scalp, hair, mucous membranes and/or nails. The gel composition is particularly suited for treating sensitive skin and scalp, as well as for moisturizing the skin. Sensitive skin is described in EP-A-680749, incorporated herein by reference. The composition may also be used to combat the visible signs aging. The gel composition is applied to the skin, scalp, hair, mucous membranes and/or nails of a subject. The subject is preferably a human subject. Preferably, the amount of composition applied is sufficient to coat the skin, scalp, hair, mucous membranes and/or nails of the subject. The composition may be applied as necessary. Preferably, the composition is applied once or twice a day.

The gel composition is prepared using procedures well-known to those of ordinary skill in the art. When the gel contains only an aqueous phase, the components are preferably mixed and stirred until a homogeneous gel is obtained. Heat may be used if desired. When the gel addtionally contains hydrophobic components, i.e., an oily phase or dispersed oils, the aqueous phase and the hydrophobic components are preferably prepared separately and then mixed together. The aqueous phase may be added to the oily phase or oils to be dispersed therein. Alternatively, the oily phase or oils may be added to the aqueous phase. After combining the aqueous phase and the hydrophobic materials, the resulting mixture is preferably stirred to homogeneity to produce the gel.

The composition may also be used to manufacture other cosmetic, pharmaceutical and/or dermatological agents for treating sensitive skin, sensitive scalp and/or for moisturizing the skin.

EXAMPLES

Having generally described this invention, a further understanding can be obtained by reference to certain specific examples which are provided herein for purposes of illustration only and are not intended to be limiting unless otherwise specified. The quantities listed are % by weight.

Example 1

Moisturizing gel

| | |
|---|---|
| Strontium chloride.6H$_2$O | 6% |
| Glycolic acid | 1% |
| Glycerin | 5% |
| Cetylhydroxyethyl cellulose (POLYSURF 67 from Aqualon Company) | 1% |
| Perfume | 0.2% |
| Perfume peptizing agent | 1% |
| D-panthenol | 1% |
| Sodium salt of pyrrolidonecarboxylic acid | 1.5% |
| Preservative | 0.2% |
| Demineralized water qs | 100% |

The gel obtained had a smooth appearance and was pleasant to apply. It was effective in moisturizing the skin, especially sensitive skin.

Example 2

Anti-aging day cream

Oily phase:

| Hydrogenated isoparaffin | 10% |
|---|---|
| Cyclomethicone | 10% |
| Cetyl alcohol | 1% |
| 5-n-Octanoylsalicylic acid | 0.2% |

Aqueous phase:

| Calcium nitrate tetrahydrate | 6% |
|---|---|
| Cetylhydroxyethyl cellulose (POLYSURF 67 from Aqualon Company) | 1.5% |
| Preservative | 0.2% |
| Demineralized water qs | 100% |

This composition was prepared by mixing the components of the aqueous phase with heat, stirring until homogeneous, introducing, with stirring, the previously homogenized oily phase and stirring until homogeneous. The resulting cream was white, soft on application and capable of treating the skin of the face, particularly extremely sensitive skin.

Example 3

Moisturizing day cream

Oily phase:

| Pentaerythrityl tetraethylhexanoate | 0.45% |
|---|---|
| Cetyl alcohol | 0.075% |
| Copra fatty acid diethanolamine | 0.075% |
| ARLACEL 165 (ICI Surfactants) | 0.28% |

Aqueous phase:

| Anhydrous calcium chloride | 2.8% |
|---|---|
| Glycolic acid | 0.5% |
| Cetylhydroxyethyl cellulose (POLYSURF 67 from Aqualon Company) | 1% |
| Glycerin | 3% |
| Demineralized wate qs | 100% |

This composition was manufactured by separately preparing the two phases and then introducing the oily phase into the aqueous phase, with stirring. The cream obtained was white cream and moisturized the skin.

Example 4

Moisturizing day cream

A cream identical to that of Example 3 was prepared using 10% calcium chloride instead of 2.8%. A stable gelled cream capable of moisturizing the skin was obtained.

Example 5

Anti-aging cream (oil-in-water emulsion)

Oily phase:

| Hydrogenated isoparaffin | 10% |
|---|---|
| Cyclomethicone (DC 245 from the Dow Corning Company) | 10% |
| Cetyl alcohol | 4% |
| Sorbitan tristearate (SPAN 65 from ICI Surfactants) | 0.9% |
| PEG-40 Stearate (MYRJ 52 from ICI Surfactants) | 2% |

Aqueous phase:

| Strontium chloride.6$H_2O$ | 6% |
|---|---|
| Lactic acid | 5% |
| Cetylhydroxyethyl cellulose (POLYSURF 67 from Aqualon Company) | 0.7% |
| Demineralized water qs | 100% |

The procedure for preparing this composition consisted of preparing the two phases separately until homogeneous and in introducing the oily phase into the aqueous phase, with stirring. The resulting cream was stable and was useful for treating facial skin, particularly very sensitive skin.

Example 6

Anti-aging cream (water-in-oil emulsion)

Oily phase:

| Cetyl dimethicone copolyol (ABIL EM-90 from Goldschmidt Chemical) | 3% |
|---|---|
| Cyclomethicone (DC 245 from by the Dow Corning Company) | 12% |
| Silicone gum (DC 1403 from the Dow Corning Company) | 3% |
| Apricot oil | 3% |

Aqueous phase:

| Strontium chloride.6$H_2O$ | 6% |
|---|---|
| Glycolic acid | |
| Cetylhydroxyethyl cellulose (POLYSURF 67 from Aqualon Company) | 5% |
| Demineralized water qs | 100% |

The procedure for preparing this composition consisted of preparing the two phases separately until homogeneous and introducing the aqueous phase into the oily phase, with stirring. The resulting cream was stable and capable of treating facial skin, even sensitive skin.

Obviously, numerous modifications and variations of the present invention are possible in light of the above teachings. It is therefore to be understood that within the scope of the appended claims, the invention may be practiced otherwise than as specifically described herein.

This application is based on French patent application No. 96-00742, incorporated herein by reference.

What is Claimed as New and Desired to be Secured by Letters: Patent of the United States is:

1. A gel composition, comprising:
    at least one cosmetic and/or dermatological active agent selected from the group consisting of α-hydroxy acids, β-hydroxy acids, α-keto acids and β-keto acids;
    at least one electrolyte;
    cetylhydroxyethyl cellulose; and water.

2. The composition of claim 1, wherein said composition is a topical composition.

3. The composition of claim 1, comprising 0.1 to 10% by weight of said cetylhydroxyethyl cellulose.

4. The composition of claim 1, comprising 0.5 to 40% by weight of said electrolyte.

5. The composition of claim 1, comprising 0.5 to 40% by weight of said electrolyte and 0.1 to 10% by weight of said cetylhydroxyethyl cellulose.

6. The composition of claim 1, wherein said electrolyte comprises a salt of a monovalent, divalent or trivalent metal ion.

7. The composition of claim 1, wherein said electrolyte comprises a metal ion selected from the group consisting of barium, calcium, strontium, sodium, potassium, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon, selenium and mixtures thereof.

8. The composition of claim 1, wherein said electrolyte comprises a strontium or neodymium salt.

9. The composition of claim 1, wherein said electrolyte comprises an anion selected from the group consisting of chloride, borate, bicarbonate, carbonate, nitrate, hydroxide, sulphate, glycerophosphate, acetate, a carboxylate of an α-hydroxy acid, a carboxylate of a fruit acid, a carboxylate of an amino acid and mixtures thereof.

10. The composition of claim 1, wherein said electrolyte comprises a salt selected from the group consisting of calcium nitrate, magnesium nitrate, strontium nitrate, calcium borate, magnesium borate, calcium chloride, magnesium chloride, sodium chloride, strontium chloride, neodymium chloride, manganese chloride, magnesium sulfate, calcium sulfate, calcium acetate, magnesium acetate and mixtures thereof.

11. The composition of claim 1, wherein said active agent is selected from the group consisting of citric acid, malic acid, glycolic acid, tartaric acid, mandelic acid, lactic acid and salicylic acid and derivatives thereof.

12. The composition of claim 1, comprising 0.001 to 30% by weight of said active agent.

13. A gel composition comprising:

0.001 to 30% by weight of a cosmetic and/or dermatological active agent selected from the group consisting of citric acid, malic acid, glycolic acid, tartaric acid, mandelic acid, lactic acid and salicylic acid and derivatives thereof;

0.5 to 40% by weight of an electrolyte comprising a strontium or neodymium salt;

0.1 to 10% by weight of cetylhydroxyethyl cellulose; and water.

14. The composition of claim 1, further comprising a dispersed oil.

15. The composition of claim 14, comprising 0.1 to 2% by weight of said dispersed oil.

16. The composition of claim 1, further comprising an oily phase.

17. The composition of claim 16, comprising 5 to 50% by weight of said oily phase.

18. A method of treating of the skin, scalp, hair, mucous membranes and/or nails, comprising applying a gel composition of claim 1 to the skin, scalp, hair, mucous membranes and/or nails of a subject.

19. A process of manufacturing the gel composition of claim 1 comprising:

mixing said at least one cosmetic and/or dermatological active agent, at least one electrolyte, cetylhydroxyethyl cellulose and water to produce the gel.

20. A method of treating of the skin, scalp, hair, mucous membranes and/or nails, comprising applying the gel composition of claim 13 to the skin, scalp, hair, mucous membranes and/or nails of a subject.

21. A process of manufacturing the gel composition of claim 13, comprising mixing said cosmetic and/or dermatological active agent, electrolyte, cetylhydroxyethyl cellulose and water to produce the gel.

* * * * *